(12) United States Patent
Kerr et al.

(10) Patent No.: US 10,143,546 B2
(45) Date of Patent: *Dec. 4, 2018

(54) POROUS IMPLANT MATERIALS AND RELATED METHODS

(71) Applicant: DePuy Synthes Products, Inc., Raynham, MA (US)

(72) Inventors: Sean H. Kerr, Oreland, PA (US); David Armbruster, West Chester, PA (US); Ami Saheba Joshi, East Providence, RI (US); James Dwyer, West Chester, PA (US); Ali Cem Recber, Coatesville, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/995,316

(22) Filed: Jan. 14, 2016

(65) Prior Publication Data

US 2016/0128823 A1 May 12, 2016

Related U.S. Application Data

(63) Continuation of application No. 13/756,636, filed on Feb. 1, 2013, now Pat. No. 9,254,193.

(Continued)

(51) Int. Cl.
*A61F 2/02* (2006.01)
*A61F 2/28* (2006.01)
(Continued)

(52) U.S. Cl.
CPC .............. *A61F 2/02* (2013.01); *A61F 2/28* (2013.01); *A61F 2/2875* (2013.01); *A61L 27/16* (2013.01);
(Continued)

(58) Field of Classification Search
None
See application file for complete search history.

(56) References Cited

U.S. PATENT DOCUMENTS 3,992,725 A 11/1976 Homsy
4,351,069 A 9/1982 Ballintyn et al.
(Continued)

FOREIGN PATENT DOCUMENTS

CN 101249277 A 8/2008
EP 1186309 A1 3/2002
(Continued)

OTHER PUBLICATIONS

International Patent Application No. PCT/US2013/024259: International Search Report dated Jun. 5, 2013, 13 pages.

*Primary Examiner* — David H Willse
*Assistant Examiner* — Javier Blanco
(74) *Attorney, Agent, or Firm* — Baker & Hostetler LLP

(57) ABSTRACT

Provided are porous, biocompatible implant bodies and materials. These materials suitably comprise a population of randomly arranged and entangled thermoplastic constituents, with at least some of the constituents being bonded to one another The implant bodies are capable of being manipulated at room temperature from a first shape to a second shape, and of maintaining the second shape at about internal body temperature. Also provided are related methods of fabricating such implants and installing the implants into a subject.

15 Claims, 13 Drawing Sheets

Related U.S. Application Data

(60) Provisional application No. 61/597,360, filed on Feb. 10, 2012.

(51) Int. Cl.
*A61L 27/16* (2006.01)
*A61L 27/56* (2006.01)
*A61B 17/80* (2006.01)
*A61F 2/30* (2006.01)

(52) U.S. Cl.
CPC ........... *A61L 27/56* (2013.01); *A61B 17/8085* (2013.01); *A61F 2002/30009* (2013.01); *A61F 2002/30011* (2013.01); *A61F 2002/30736* (2013.01); *A61F 2210/0071* (2013.01); *A61F 2210/0076* (2013.01); *A61L 2430/02* (2013.01)

(56) References Cited

U.S. PATENT DOCUMENTS

| | | | |
|---|---|---|---|
| 4,454,612 A | 6/1984 | McDaniel et al. | |
| 4,643,940 A * | 2/1987 | Shaw | C08J 9/0085 428/308.4 |
| 4,944,974 A | 7/1990 | Zachariades | |
| 5,834,113 A | 11/1998 | Shalaby et al. | |
| 6,031,148 A | 2/2000 | Hayes et al. | |
| 6,551,608 B2 | 4/2003 | Yao | |
| 7,655,047 B2 | 2/2010 | Swords | |
| 7,923,512 B2 | 4/2011 | King et al. | |
| 2001/0011190 A1 | 8/2001 | Park | |
| 2001/0018614 A1 | 8/2001 | Bianchi | |
| 2006/0073181 A1* | 4/2006 | Kuboki | A61C 8/0006 424/422 |
| 2006/0217813 A1 | 9/2006 | Posnick et al. | |
| 2006/0224242 A1 | 10/2006 | Swords et al. | |
| 2007/0093912 A1 | 4/2007 | Borden | |
| 2013/0030340 A1* | 1/2013 | Vincent | B01D 39/163 602/42 |

FOREIGN PATENT DOCUMENTS

| | | |
|---|---|---|
| JP | 62-500598 | 3/1987 |
| JP | 2008-245775 | 10/2008 |
| WO | WO 86/02656 | 5/1986 |
| WO | WO 2011/107807 | 9/2011 |
| WO | WO 2013/119458 | 8/2013 |

* cited by examiner

POROUS IMPLANT MATERIALS AND RELATED METHODS

CROSS REFERENCE TO RELATED APPLICATIONS

This application is a continuation application of U.S. patent application Ser. No. 13/756,636, filed Feb. 1, 2013, now U.S. Pat. No. 9,254,193, which claims the benefit of U.S. patent application 61/597,360, filed on Feb. 10, 2012, the contents of which are incorporated herein by reference in their entireties.

TECHNICAL FIELD

The present invention relates to the field of biomedical implants.

BACKGROUND

Orthopedic implants fabricated from porous high density or ultrahigh molecular weight polyethylene (HDPE or UHMWPE) are currently in use clinically for augmenting or replacing bone, typically in the craniofacial skeleton. These products are generally manufactured by melt fusing or sintering generally spherical particles of polymer with a controlled diameter range to form a porous solid. One advantage of porous polyethylene is that the pores allow ingrowth of soft tissue into the material after implantation, which anchors the material in place and integrates it into the body. Polyethylene also has material properties (e.g., density, flexibility) that are similar to native soft tissue.

One limitation of these implants is that while they are flexible, and can be easily bent to match the contour of the bone, they do not easily take a permanent bend. These implants are also easily cracked if bent too far, since the melt points bonding the particles of polymer together are the weak points of the structure. Because of the porosity, the porous material is also in general more flexible than a solid polyethylene shape of similar dimensions. This tends to limit the potential applications of the material to sites where significant rigidity or strength is not required.

One solution to these limitations has been to incorporate a titanium mesh into the porous polyethylene. The titanium mesh improves strength and ductility of the composite material, but the presence of a metal component is undesirable when x-ray or MRI imaging of the implant site is required. There is therefore a need for an improved implant material with similar tissue compatibility to current porous polyethylene implants, but with increased strength and the ability to be bent to shape intraoperatively in the absence of metal or other reinforcement materials.

SUMMARY

In meeting the described challenges, the present disclosure first provides biocompatible implants, the implants suitably comprising a porous body comprising a plurality of randomly arranged thermoplastic constituents, at least some of the thermoplastic constituents having an aspect ratio in the range of from greater than 1 to about 1000, at least some of the thermoplastic polymer constituents being bonded to other thermoplastic constituents at multiple sites, the porous body being capable of manipulation at room temperature from a first shape to a second shape and maintaining the second shape at about internal body temperature.

The present disclosure also provides methods of forming a biocompatible implant, the methods comprising heating thermoplastic constituents disposed in a mold so as to bond at least some of the thermoplastic constituents to one another; and applying pressure to the thermoplastic constituents so as to form an implant comprising a porous body of bonded thermoplastic constituents.

Also provided herein are methods of forming a biocompatible implant, comprising contacting a plurality of polymer constituents with at least one solvent capable of dissolving or swelling the polymer constituents so as to soften the constituents; removing the at least one solvent; and applying pressure to the plurality of polymer constituents in order to form an implant having a porous body of bonded polymer constituents.

This disclosure also provides methods of introducing an implant into a mammal, comprising selecting a location within a mammal for implant introduction; and installing an implant according to claim A to the selected location.

Also disclosed are methods of applying an implant to a targeted anatomical location, comprising manipulating an implant body according to claim A such that the implant body substantially conforms to the shape of a targeted anatomical location; and installing the implant body at the targeted anatomical location.

Further disclosed are biocompatible implants, comprising a porous body comprising a plurality of randomly arranged thermoplastic constituents, at least some of the thermoplastic constituents being elongate in shape, being irregular in shape, or both, at least some of the thermoplastic polymer constituents being bonded to other thermoplastic constituents at multiple sites, the porous body being capable of manipulation at room temperature from a first shape to a second shape and maintaining the second shape at about internal body temperature.

Additionally provided are biocompatible implants, comprising a porous body comprising a plurality of randomly arranged thermoplastic filaments, at least some of the thermoplastic filaments being bonded to other thermoplastic filaments at multiple sites, the porous body being capable of manipulation at room temperature from a first shape to a second shape and maintaining the second shape at around about internal body temperature.

Further provided are biocompatible implants, comprising a porous body formed from a plurality of randomly arranged thermoplastic constituents bonded to one another under heating, at least some of the thermoplastic constituents having an aspect ratio in the range of from greater than 1 to about 1000, the porous body being capable of manipulation at room temperature from a first shape to a second shape and maintaining the second shape at about internal body temperature.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification, including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Any and all documents cited in this application are incorporated herein by reference in their entireties.

In a first aspect, the present disclosure relates to biocompatible implants. The implants include a porous body comprising a plurality of randomly arranged thermoplastic constituents, with at least some of the thermoplastic polymer constituents being bonded to other thermoplastic constituents at multiple sites.

Figure 1:
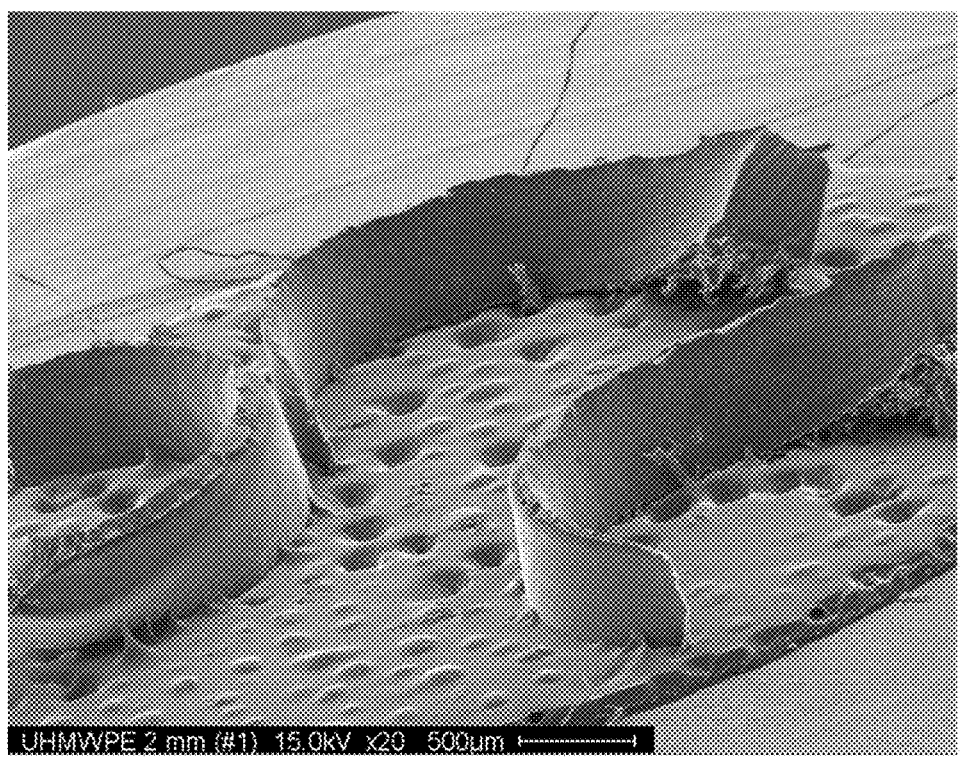
FIG. 1 illustrates a SEM image of several elongated chips of UHMWPE made by machining from a solid block of polymer with an end mill.
Figure 2:
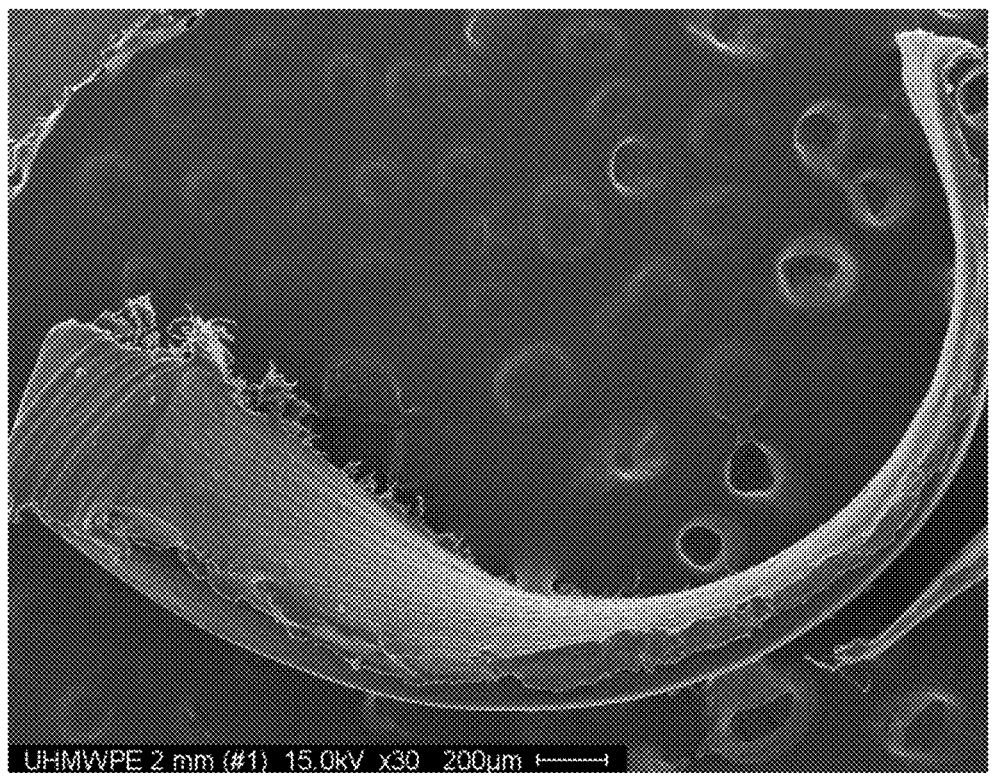
FIG. 2 illustrates, for a PE milling chip at 30×, a SEM image of a single elongated chip of UHMWPE made by machining from a solid block of polymer with an end mill.

It should be understood that the term "constituent" may refer to an amount of polymer present in a variety of shapes. For example, a constituent may be a fiber having a traditionally cylindrical form and having a constant cross-sectional dimension (e.g., diameter). A constituent may also be an elongated particle (e.g., oblong or even football-shaped). A constituent may have an irregular geometry. For example, a constituent may have one end that is larger (e.g., wider) than the other. A constituent may have an aspect ratio (i.e., ratio of major axis to minor axis) in the range of 1, more than 1, 10, 100, or even 1000. A constituent may be flattened (e.g, plate-like or pancake-like) in configuration. The constituent may, in some embodiments, be spun or extruded fibers. The fibers may be cut to the same length or to different lengths. Filaments that are produced by a lathe or other milling machines may also be used. For example, FIG. 1 illustrates, for a PE milling filament at 20×, a SEM image of several elongated chips of UHMWPE made by machining from a solid block of polymer with an end mill. These chips are made by the end mill slicing a section off the solid block, which imparts a curve to the material in the process. FIG. 2 illustrates, for a PE milling chip at 30×, a SEM image of a single elongated chip of UHMWPE made by machining from a solid block of polymer with an end mill.

Figure 12:
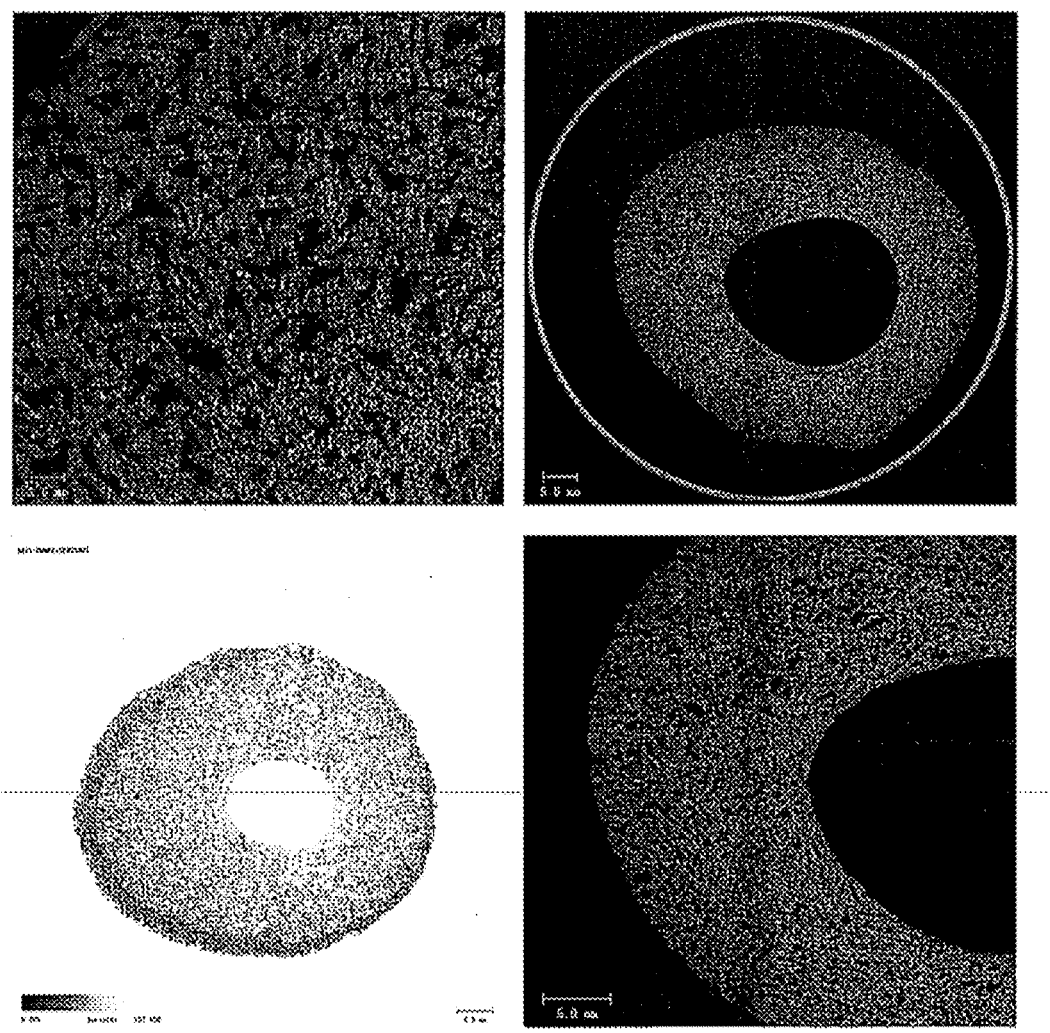
FIG. 12 illustrates four micro-CT images of samples of a porous polyethylene cranial implant made from filaments as shown in FIG. 2.

FIG. 12 presents four micro-CT images of samples of a porous polyethylene cranial implant made from filaments similar to that shown in FIG. 2. The dark areas are voids, and the lighter areas are polyethylene. These figures indicate a uniform porosity extending through the full thickness of the sample. The central void shown in the top right, bottom left, and bottom right figures is an artifact of the scanning method. The scan is a slice through a dome-shaped implant, parallel to its base, and the center of the dome was not captured.

Figure 13:
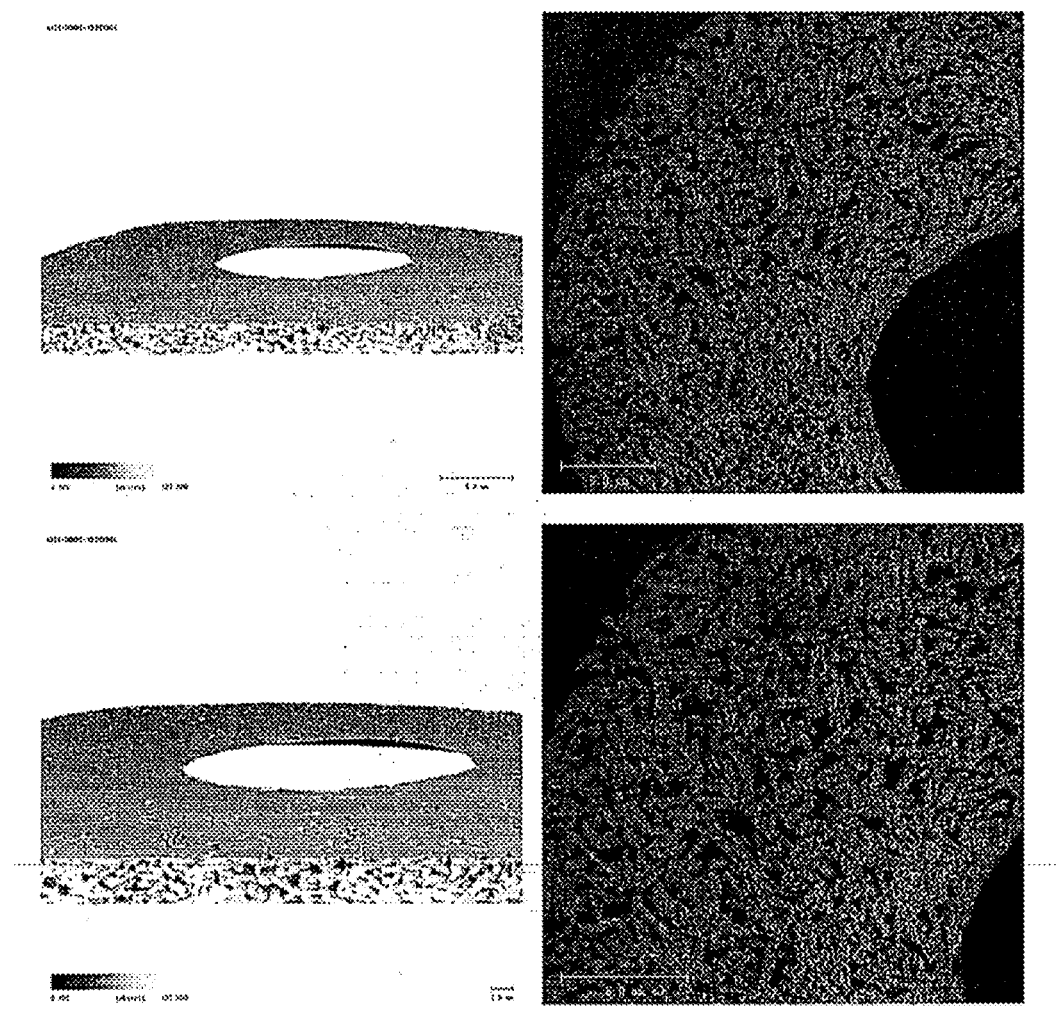
FIG. 13 illustrates four micro-CT images of samples of a porous polyethylene cranial implant made from filaments as shown in FIG. 2.

FIG. 13 shows four micro-CT images of samples of a porous polyethylene cranial implant made from fibers as shown in FIG. 2. The dark areas are voids, and the lighter areas are polyethylene polymer. These figures illustrate an essentially uniform porosity that extends through essentially the full thickness of the sample. The disclosed materials, however, need not necessarily possess a uniform porosity throughout. The top left and bottom left images show a slice through the sample in a vertical plane, which images show a continuous uniform porosity extending through the full thickness of the sample. The round central void shown in the figures is an artifact of the scanning method. The scan is a slice through a dome-shaped implant, parallel to its base, and the center of the dome was not captured. The chart following FIG. 13 indicates that the sample had a measured porosity of about 37%, as provided in the data table below:

| SampName | SampNo | MeasNo | TV (mm3) | BV (mm3) | BV/TV | Porosity(%) |
|---|---|---|---|---|---|---|
| AS11-UHMPE-TESTING1 | 783 | 1003 | 2893.558 | 1816.584 | 0.6278 | 37.22 |

As described elsewhere herein, the porous bodies may comprise constituents that differ from one another in size, shape, or even composition. For example, a body may comprise some constituents that are fibers and also some constituents that are platelets. It should be understood that the present materials present advantages over existing materials that are formed of spherical particles that are bound to one another. The constituents of the present disclosure suitably have an aspect ratio that is greater than 1. For example, a constituent may be football-like in configuration, and may exhibit an aspect ratio of 1.5, 2, 5, 10, or even 50 or 100, or more. An aspect ratio of 200, 300, or 500 may be suitable for constituents used in the disclosed materials. The plurality of constituents in a material according to the present disclosure may be entirely free of the generally spherical particles conventionally used in the prior art, or may be essentially free of spherical particles, i.e., may be 95, 96, 97, 98, 99, or even 99.99 percent free of such generally spherical particles.

It should also be understood that constituents used in the disclosed materials may be irregular in shape. For example, a constituent may be lopsided, ridged, rough, rhomboid, or otherwise asymmetric. As described elsewhere herein, a constituent may be elongate in shape, such as a fiber, a rice grain shape, a football shape, and the like. Constituents may be elongate and irregular, as shown by the filament in FIG. 2.

In one exemplary embodiment, the body may include fiber constituents that are bonded to one another, which bonding may be accomplished by heating the constituents so as to form a plurality of constituents bonded to one another. Bonding constituents to one another allows for the constituents to have multiple attachment points, particularly in the case where the constituents (e.g., fibers) are randomly oriented relative to one another. In some embodiments, the constituents (e.g., fibers) may be entangled with one another. Without being bound to any particular theory, the increased number of contact points between adjacent constituents and, where present, entanglement between adjacent constituents, enhances the mechanical properties of the disclosed materials. The random arrangement confers desirable mechanical properties on the disclosed implants, particularly in comparison to other structures formed from oriented or otherwise anisotropic fibers or other constituents.

Suitable thermoplastic constituent materials include polyethylene, in particular ultra high molecular weight polyethylene, although other polyethylenes (e.g., HDPE, LDPE) are suitable. Polyethylene has properties (e.g., density, flexibility, thermal conductivity) that are similar to those of natural soft tissue, which in turn makes polyethylene a particularly suitable material for implantation. Other suitable thermoplastics include PEEK (polyether ether ketone), PEKK (polyetherketoneketone), PAEK (polyaryletherketone), PLA (polylactic acid), PGA (polyglycolic acid), PLGA copolymers, polypropylene, polycaprolactone, polyphenylene, polyphenylsulfone, PET (polyethylene tetephthalate), polyurethane, polyamide, polymethyl methacrylate, polycarbonate, or other biocompatible polymers.

The porous body is capable of being manipulated (e.g., by hand) at, for example, room temperature from a first shape to a second shape, with the porous body further being capable of maintaining the second shape at about, for example, room temperature. A body according to the present disclosure also suitably maintains the second shape at or even at above internal body temperature, which may be around 90, 95, 100, 105, or even around 110 or 120 deg F., in some cases. This characteristic renders the materials especially suitable for implant use, as the user (e.g., surgeon or other medical personnel) may bend, curve, or otherwise shape the material by hand before or even during an operative procedure. The user may also use various shaping implements (such as bending jigs, molds, and the like) to assist with shaping the porous body. Because of this characteristic, the user has the capability to shape and reshape the material during the procedure so as to achieve an optimal implant shape.

A user may alternatively apply heat to the implant body to facilitate shaping or molding the body. The heat may be applied so as to soften the implant body or some region of the body to facilitate bending, cutting, or otherwise shaping the body. The materials may be cut with a knife, saw, scissors, or other standard surgical instruments. Heat may, depending on the user's needs, be applied to the body so as to facilitate adjustment of the body once the implant body has been installed or implanted into or even onto the subject. Such heat may, in some embodiments, be applied by contacting the implant body with a heater or other heating element so as to apply the heat at the implant and avoid heating tissue or other parts of the subject that are in close proximity to the implant.

The porous body is suitably in the form of a sheet or other planar or nearly planar configuration. The sheet may be circular, square, or polygonal, or even irregular in shape. The bodies need not necessarily be sheets, as cylindrical, spherical, oblong, elongate, and other porous body shapes are all within the scope of the present disclosure. The body may be irregular or curved in form, and may be shaped so as to approximate the shape of a bone or other material being replaced. Alternatively, the body may be shaped so as to be shaped for insertion into a defect, space, or injury site. The porous body may define a thickness in the range of from about 1 mm to about 10 mm. Thicknesses in the range of from about 3 mm to about 5 mm are considered especially suitable.

Because these materials are capable of being shaped into a particular configuration and then maintain that configuration, the materials may, in some embodiments, be used as standalone implants, i.e., they can be implanted directly into a patient without further reinforcement. This represents a departure from existing implant alternatives that may require reinforcement with a metallic mesh or use with other stiff or rigid implant materials or layers. The constituent based implants of the current disclosure have advantageous mechanical properties, such as bending strength, stiffness, and resistance to cracking, without need for further reinforcement.

The disclosed materials may exhibit a range of mechanical properties. In some embodiments, a material according to the present disclosure may have an intrusion volume (expressed in mL/g of mercury intrusion, and according to the ISO 15901-1:2005 standard) in the range of from about 0.1 to about 0.8 or even about 0.9, or from about 0.2 to about 0.7, or even from about 0.3 to about 0.6. A material according to the present disclosure may have a percentage of solids (by volume of solids per volume of material) in the range of from about 10% to about 90%, of from about 20% to about 80%, of from about 30% to about 70%, or even of from about 40% to about 60%. As described elsewhere herein, UHWMPE is considered an especially suitable material from which to form the disclosed materials.

A sample according to the present disclosure and having a thickness in the range of from about 3 mm to about 4 mm may have a tensile strength in the range of from about 2 MPa to about 7 MPa, or from about 3 MPa to about 6 MPa, or even from about 4 MPa to about 6 MPa. The sample may also have a tensile strength—normalized based on the percentage of solid structure of the sample—in the range of from about 5 MPa to about 15 MPa, of from about 7 MPa to about 13 MPa, or even of from about 9 MPa to about 10 MPa.

A sample according to the present disclosure and having a thickness in the range of from about 3 mm to about 4 mm may have a tensile modulus in the range of from about 100 MPa to about 350 MPa, of from about 150 MPa to about 250 MPa, or even of from about 200 MPa to about 225 MPa. The sample may also have a tensile modulus—normalized based on the percentage of solid structure of the sample—in the range of from about 300 MPa to about 600 MPa, of from about 400 MPa to about 500 MPa, or even of from about 450 MPa to about 475 MPa.

A sample according to the present disclosure and having a thickness in the range of from about 3 mm to about 4 mm may have a flexural strength in the range of from about 3 MPa to about 10 MPa, or from about 4 MPa to about 8 MPa, or even of from about 5 MPa to about 6 MPa. The sample may also have a flexural strength—normalized based on the percentage of solid structure of the sample—in the range of from about 5 MPa to about 25 MPa, of from about 7 MPa to about 20 MPa, or even of from about 9 MPa to about 15 MPa.

A sample according to the present disclosure and having a thickness in the range of from about 3 mm to about 4 mm may have a flexural modulus in the range of from about 100 MPa to about 350 MPa, of from about 150 MPa to about 250 MPa, or even of from about 200 MPa to about 225 MPa. The sample may also have a flexural modulus—normalized based on the percentage of solid structure of the sample—in the range of from about 250 MPa to about 600 MPa, of from about 300 MPa to about 500 MPa, or even of from about 450 MPa to about 475 MPa.

A user may, for example, shape the porous body into a shape that corresponds to a bone contour or a shape otherwise effective for the intended purpose of the implant. The materials may be used to replace virtually any bone anywhere in the skeleton, but do have particular application to the craniofacial region. The disclosed materials may also be used as spinal interbody spacers or even as spacers for addressing segmental defects in long bones. The disclosed materials may also be used to replace cartilage, such as costal cartilage of the ribs. A sheet of the disclosed materials may be used to replace a portion of the chest wall in a patient.

The pores present in the materials allow ingrowth of soft tissue, bone, or other body tissue into the material after implantation. This ingrowth in turn anchors the material in place and integrates the material into the body.

In some embodiments, at least some portion (e.g., a region of the surface) of a constituent may be hydrophilic. It will be understood that the term "hydrophilic" is used here to refer to a modified thermoplastic that is more hydrophilic than similar, "untreated" thermoplastic. The thermoplastic (e.g., UHMWPE) can be made hydrophilic by any suitable means, for example, the thermoplastic may include functional groups attached to at least a portion thereof.

The hydrophilic functional groups can be directly attached to at least a portion of the thermoplastic, or the hydrophilic functional groups can be part of hydrophilic monomers attached to at least a portion of the thermoplastic. Preferably, the hydrophilic functional groups comprise one or more functional groups selected from the group consisting of amino functional groups, carboxylic acid functional groups, hydroxyl functional groups, hydroxysulfuryl functional groups, and combinations thereof More preferably, the hydrophilic functional groups comprise one or more carboxylic acid functional groups. Suitable hydrophilic monomers that can be used to modify the surface of the ultrahigh molecular weight polyethylene or other thermoplastic include, but are not limited to, acrylic acid, poly(ethylene glycol), 2-hydroxyethyl methacrylate, and combinations thereof.

Without being bound to any particular theory, the porous and/or hydrophilic nature of the thermoplastic provides a useful substrate for supporting bone and/or soft tissue ingrowth, as well as (if need be) the penetration of bone cement or other fixative into the implant material. Cells (such as bone cells, or tissue cells) can attach themselves to the porous surface of the thermoplastic, particularly where the material has been treated to render it hydrophilic, as the hydrophilic portions provide regions for cell attachment.

The porous nature of the materials may also, depending on the user's needs, provide an enhanced medium for bone cement to penetrate into the implant, e.g., into the network of pores that extends into the implant. This in turn improves the ability of the cement to bond the implant to host bone. The pores may also serve as an enhanced medium for other material, such as growth factors, medicaments, and the like to be provided at the site of bone ingrowth into the implant body. As one example, the pores of the implant body might be coated with a medicament (e.g., an antibiotic) before the implant is installed in the subject, which would result in the antibiotic being present at the site of bone ingrowth. This may be useful in situations where, for example, there may be the potential for infection or other complications at the operative site.

The user may shape the porous material intraoperatively, before an operation, or both. The materials may be provided to the end-user in partially shaped or template form, with the end-user shaping the materials to their specific needs before or during the course of an operation. For example, a portion of material may be provided to the user in hemispheric form, with the user shaping (e.g., by bending, folding, or cutting) the hemisphere of material to conform to the target region of the patient as needed.

One may create an array of prepackaged material kits that are tailored to particular applications. For example, one may fabricate a range of implant kits, with each kit including a portion of the disclosed materials that is pre-sized or pre-shaped for a particular purpose. For example, one may create a range of craniofacial implant body kits, with different kits containing implant bodies that are pre-sized or pre-shaped for implantation into large, medium, and smaller individuals. This approach may reduce the amount of operative shaping that must be performed by the end-user of the implant, as the end user may receive or select from a kit an implant that is relatively close to the desired final form.

The disclosed implants may also include, in some embodiments, a non-porous material bonded to the porous body. Thermoplastic sheets are considered especially suitable for this purpose, in particular thermoplastic sheets that comprise polyethylene, especially ultra high molecular weight polyethylene. Other materials may be used for the nonporous sheet, and there is no requirement that the porous body and nonporous sheet be of the same material. The nonporous material may define a cross-sectional dimension (e.g., thickness) in the range of from about 1 micrometer to about 5 mm, or even from about 10 micrometers to about 5 mm. Thicknesses in the range of from 0.1 mm to about 0.5 mm or even about 1 mm are considered especially suitable.

Figure 3:
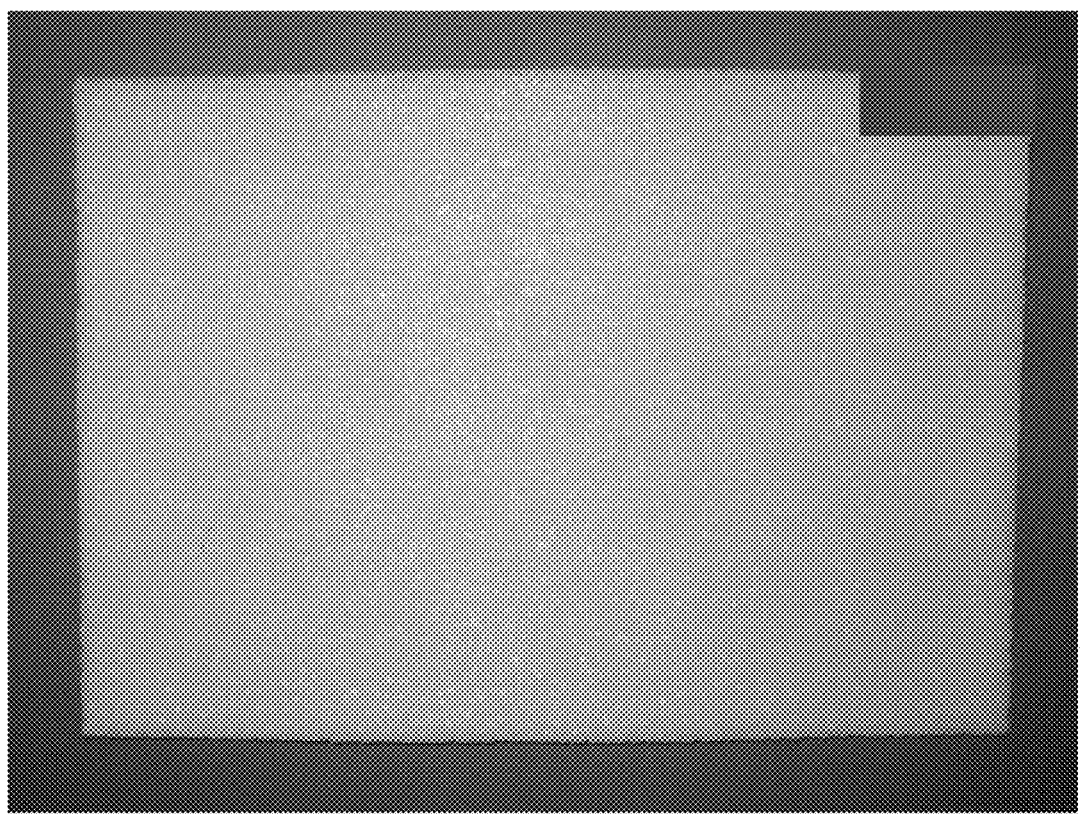
FIG. 3 illustrates, for an exemplary fibrous PE sheet, an image of a sheet of porous polyethylene formed by thermally bonding filaments of UHMWPE to form a porous solid.
Figure 4:
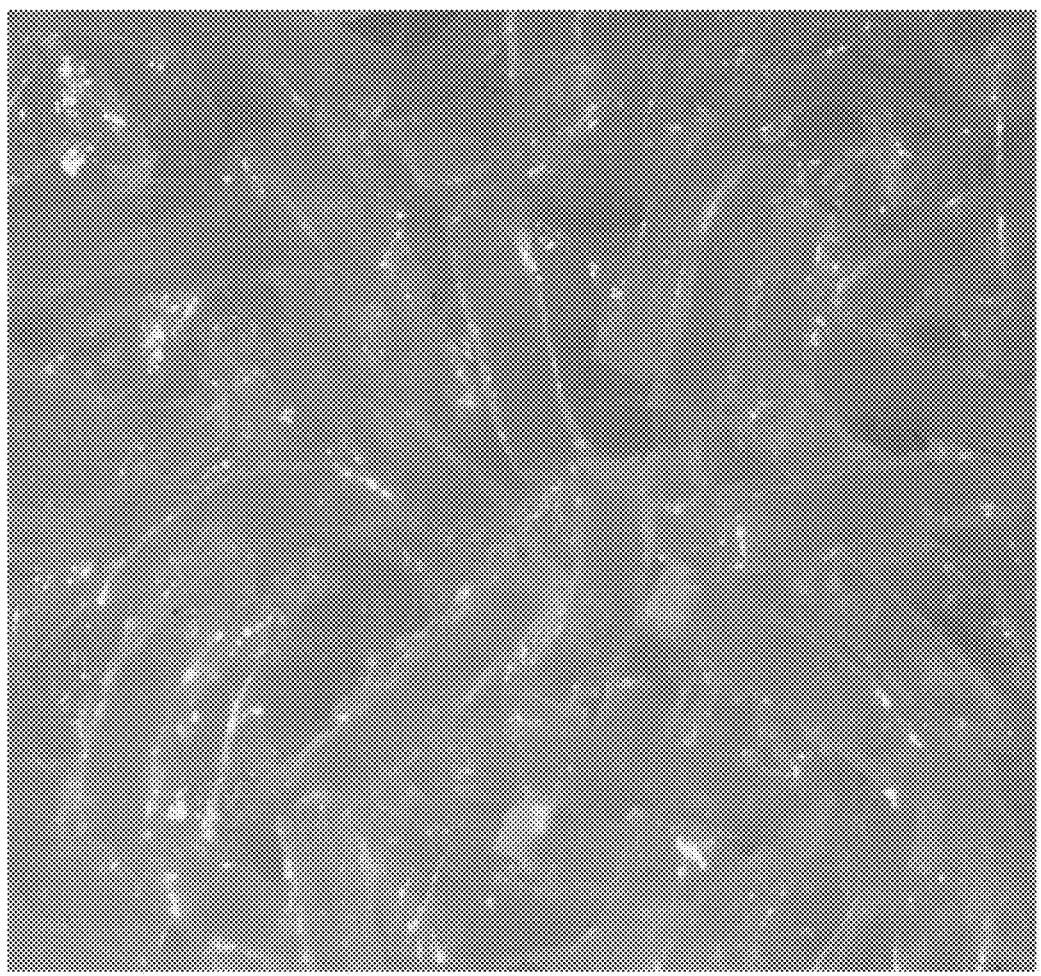
FIG. 4 illustrates, for a second exemplary fibrous PE sheet, a close-up light micrograph of the surface of the thermally bonded porous UHMWPE sheet, showing the elongated filaments.
Figure 5:
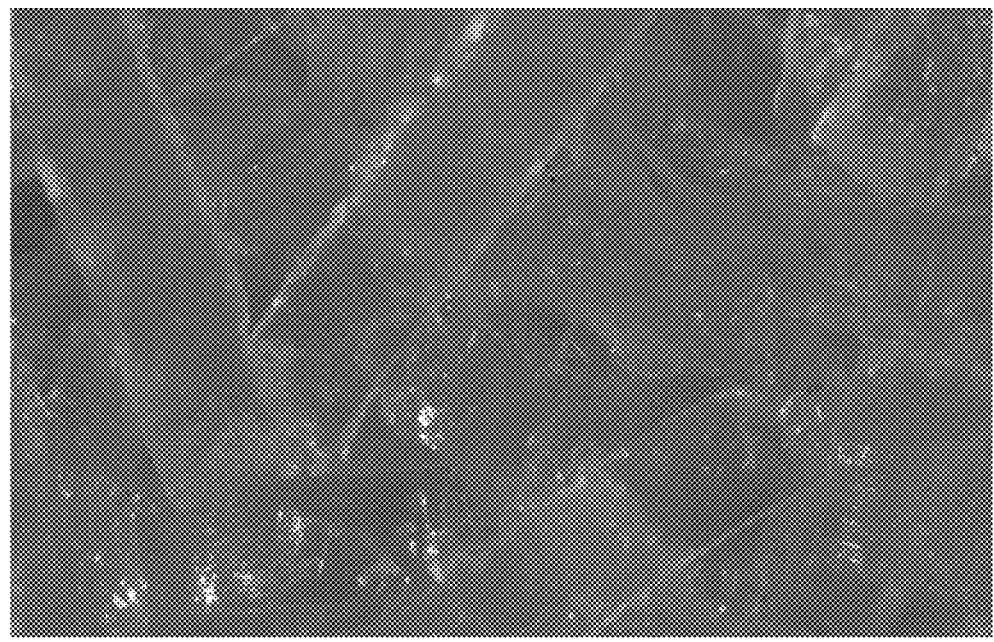
FIG. 5 illustrates, for the sheet shown in FIG. 4, a close-up light micrograph at higher magnification of the surface of the thermally bonded porous UHMWPE sheet, showing the elongated filaments.

The porous body may, in some embodiments, be characterized as having an interconnected porosity. In some embodiments, such as those where the porous body is in the form of a sheet, one or more discrete pores may place the upper and lower surfaces of the body into fluid communication with one another. In certain embodiments, the pores or interconnected pores may extend only partway through the thickness of the body. In this way, the user may fabricate a body (e.g., a sheet) that includes pores that extend partway through the material but that also include a portion (e.g., one of the sheet's faces) that is nonporous. FIG. 3 illustrates, for a fibrous PE sheet, an image of a sheet of porous polyethylene formed by thermally bonding filaments of UHMWPE to one another so as to form a porous solid, using a metal mold. The sheet shown is approximately 135 mm×195 mm by 3 mm thick.

Such a body may be fabricated by building the body up from a gradient of constituent densities. For example, the user may first place one or more layers of comparatively-widely spaced constituents at the bottom of a mold, followed by one or more layers of more closely-spaced constituents, followed by one or more layers of yet more closely-spaced constituents, and so on such that the final layer of the body includes constituents that are so fine or so closely spaced that upon melting, the constituents fuse so closely together that that surface of the body is nonporous. In some applications, one may employ as a preferred design a material with consistent porosity through the thickness of the material, with a thin, nonporous layer laminated onto one surface. In some embodiments, a body may have a graded porosity where the outer surface has a more open porosity, the middle may be more dense, and the inner surface is nonporous. This may provide advantages for tissue ingrowth, mechanical properties, or bending properties. Such a material may be fabricated by thermally bonding a first sheet with open pores to a second sheet with less open pores, and bonding the second sheet to a third sheet that may be nonporous. The embodiments may be formed by bonding two, three, four, five, or more sheets to one another. Alternatively, as described elsewhere herein, a body according to the present disclosure may include a porous layer bonded to a nonporous layer.

The disclosed bodies may have a porosity in the range of from about 10% to about 70% by volume, or in the range of from about 20% to about 50% by volume, or even in the range of from about 30% to about 40% by volume. The pores may be of a range of cross-sectional dimensions (e.g., diameter, width, radius), and the pores need not all be of the same cross-sectional dimension. A body comprising pores may be configured such that the majority of the pores of the porous body have a characteristic cross-sectional dimension in the range of from about 50 micrometers to about 1000 micrometers, or in the range of from about 100 micrometers to about 500 micrometers, or even in the range of from about 200 micrometers to about 300 micrometers. The pores may be circular in cross-section, but may also be polygonal, oblong, or irregular in cross-section.

An implant may define a thickness in the range of from about 1 mm to about 10 mm, or even about 50 mm. The thermoplastic constituents of the bodies may have an average cross-sectional dimension (e.g., diameter, width, length, thickness, chord) in the range of from about 0.1 mm to about 5 mm, or in the range of from about 0.3 mm to about 1.5 mm.

The thermoplastic constituents may have an average length in the range of from about 1 mm to about 50 mm, or from about 2 mm to about 20 mm. The average aspect ratio of the thermoplastic constituents may be in the range of from about 1 to about 1000, or from 5 to about 500, or even from about 10 to about 100. A constituent may be formed from spinning, extrusion, or other methods known in the art. For example, a constituent may be formed by carving, or machining from the surface of a solid piece of material such as by a lathe or milling machine tool. The constituent may be in the form of a filament or chip from a machining process. A filament may be an elongate strip, as shown by exemplary FIG. 1, and need not necessarily be circular in cross-section, and may be flat or otherwise non-circular. These portions or segments may be formed by cutting (e.g. with a knife, scalpel, or even scissors), melting, or otherwise segmenting a constituent. The constituents may be circular in cross-section, but may also be flattened, oblong, or polygonal in cross-section. The constituents also need not have flat ends (such as the ends present on a geometric cylinder), as the ends of the constituents may be rounded, tapered, or even ragged or irregular. In some embodiments, a constituent (e.g., a fiber, a chip) may be of non-uniform cross section, and may even be thicker at one end than the other. A cross-sectional dimension of the constituent may vary along the length of the constituent. Constituents may be straight, but may also be bent or curved.

The plurality of randomly arranged thermoplastic constituents may comprises a polydisperse mixture of thermoplastic constituents. In such embodiments, two or more of the constituents differ from one another in length, cross-sectional dimension, and/or composition.

As one illustrative example, a body may include a first population of ultra high molecular weight polyethylene fiber constituents having an average length of about 30 mm and an average diameter of about 20 micrometers, and a second population of ultra high molecular weight polyethylene fiber constituents having an average length of about 35 mm and an average diameter of about 10 micrometers. One advantage of using a polydisperse mixture of constituents that differ in dimension but not in composition is that constituents will melt at about the same temperature, which in turn simplifies the processing of the constituents to form the disclosed implants, although it is not a requirement that all constituents in the body have the same melting temperature.

In some embodiments, the body includes constituents that differ from one another in terms of material composition. For example, a body may include filaments of UHMWPE and platelets of PEEK. A body may include constituents of two or more materials.

The bonded thermoplastic constituents of a body according to the present disclosure may be characterized as being melt bonded to one another, as melt-bonding is a particularly suitable process for forming the disclosed articles. Alternatively, the bonded thermoplastic constituents may be characterized as being solvent bonded to one another.

As mentioned, polyethylene is considered an especially suitable material for the constituents of the disclosed bodies; high density polyethylene (HDPE), ultrahigh molecular weight polyethylene (UHMWPE), medium density polyethylene (MDPE), or combinations thereof are all especially suitable. UHMWPE suitably has a molecular weight in the range of from about 3 million to about 6 million, and may have a density in the range of from about 0.930 to about 0.935 g/cc, or even about 0.945 g/cc. HDPE suitably has a density of greater or equal to about 0.914 g/cc; MDPE suitably has a density of about 0.926-0.940 g/cc.

Other polyethylenes, including ultra low molecular weight polyethylene (ULMWPE), high molecular weight polyethylene (HMWPE), high density cross-linked polyethylene (HDXLPE), cross-linked polyethylene (PEX or XLPE), linear low density polyethylene (LLDPE), low density polyethylene (LDPE), or even very low density polyethylene (VLDPE) are all considered suitable thermoplastic constituent materials.

Thermoplastic constituents may be formed from homopoymers, copolymers, or even mixtures or blends thereof. The thermoplastic constituents may comprise a polyalkene, a polyalkene copolymer, or combinations thereof.

The disclosed materials are, by virtue of their mechanical properties, capable of functioning in a stand-alone manner. By this is meant that the implants are capable of being installed and functioning within a subject without the need for additional reinforcing materials, such as metal meshes or other reinforcing or stiffening materials such as strips of plastic or other polymer. In other embodiments, reinforcing meshes, fibers, and other materials may be used with materials according to the present disclosure. An implant material may be secured to the skeleton or cranium using small plates, screws, wires, staples, cement, or with other surgical devices known to those of ordinary skill in the art. These securing devices do not serve to reinforce the implant, but instead serve to secure the implant to surrounding bone. For example, some existing implant materials include a metal mesh or other reinforcement that give rise to a rigid implant. The disclosed implants, however, need not include such reinforcing materials. Accordingly, in some embodiments, the implant consists essentially of the porous body, or of the porous body bonded to a nonporous sheet or other material.

The present disclosure also provides methods of forming a biocompatible implant. These methods include, among other things, heating thermoplastic constituents disposed in a mold so as to bond at least some of the thermoplastic constituents to one another; and applying pressure to the thermoplastic constituents in the mold so as to form an implant comprising a porous body of bonded thermoplastic constituents. As one non-limiting example, for UHMWPE, the bonding temperature could be from about 200 to about 250° C. in a Carver Press, and the processing time could be in the range of from about 6 to about 12 minutes. The user may admit cooled air or may also chill the press plates. As one of ordinary skill in the art will appreciate, the mechanical properties of the disclosed materials can vary depending on process conditions. For example, the pressure used to compact the constituents may vary depending on the weight of constituents introduced into the mold.

In some embodiments, the user may place a non-porous thermoplastic sheet atop the thermoplastic constituents so as to form an implant having a non-porous surface. In some embodiments, an implant may have two nonporous surfaces, with a porous section therebetween. For example, an implant could take the form of a porous cylinder that has nonporous ends. Alternatively, an implant may have porous surfaces with a nonporous center section. As one example, the center section may provide increased strength or rigidity to the implant. In one illustrative process, lamination of a nonporous topsheet to another, porous sheet is performed in a Carver Press, wherein one platen is set at about 230° C., with processing lasting about one minute. Pressure may be set in the range of from about 2900N/6400 mm$^2$ to about 2900N/280000 mm$^2$. The nonporous film may be pre-stress relieved before lamination.

The placement may include bonding the thermoplastic sheet to the constituents, by way of application of heat, solvent, or both. The nonporous thermoplastic sheet may be placed into the mold after heating and before applying pressure.

The non-porous thermoplastic sheet may be formed of one or more of ultra high molecular weight polyethylene, although other polyethylenes (e.g., HDPE, LDPE), PEEK, PEKK, PAEK, PLA, PGA, PLGA copolymers, polypropylene, polycaprolactone, polyphenylene, polyphenylsulfone, PET, polyurethane, polyamide, polymethyl methacrylate, polycarbonate, or other biocompatible polymers and the like. The nonporous thermoplastic sheet may define a thickness in the range of from about 0.05 mm to about 5 mm.

In one embodiment, the methods include contacting a plurality of polymer constituents with at least one solvent capable of dissolving or swelling the polymer constituents so as to soften the constituents; removing the at least one solvent; and applying pressure to the plurality of polymer constituents in order to form an implant having a porous body of bonded polymer constituents. In some embodiments, the user may remove at least a portion of the at least one solvent from the plurality of polymer constituents after the constituents have softened. For polyethylene, linear aliphatic solvents such as decane or dodecane, or aromatic solvents such as decalin, xylene, or toluene are suitable for this application. Using the solvent at an elevated temperature is considered particularly suitable.

The methods may further include placing a non-porous thermoplastic sheet into contact with the plurality of polymer constituents before the step of applying pressure so as to form an implant having a non-porous surface.

In some embodiments, the user may include a processing aid, such as a particulate ceramic material, into the constituents before mold filling and heat treatment. The processing aid may act to prevent the polymer constituents from flowing freely when heated above their melting point. The processing aid may be removed by washing the processed material with water, acid, or other appropriate solvent so as to remove the processing aid from the finished product.

The present disclosure also provides methods of introducing an implant into a subject. These methods include selecting a location within a subject or patient, e.g., a mammal, for implant introduction; and installing an implant according to the present disclosure to the selected location. In some instances, the implant may be cut or otherwise shaped to size and then bent or manipulated to fit into a bone defect, such as a cranial defect. The implant may be placed into the defect and then secured into place using sutures, metal wires, or plates and screws, as described elsewhere herein.

Figure 6:
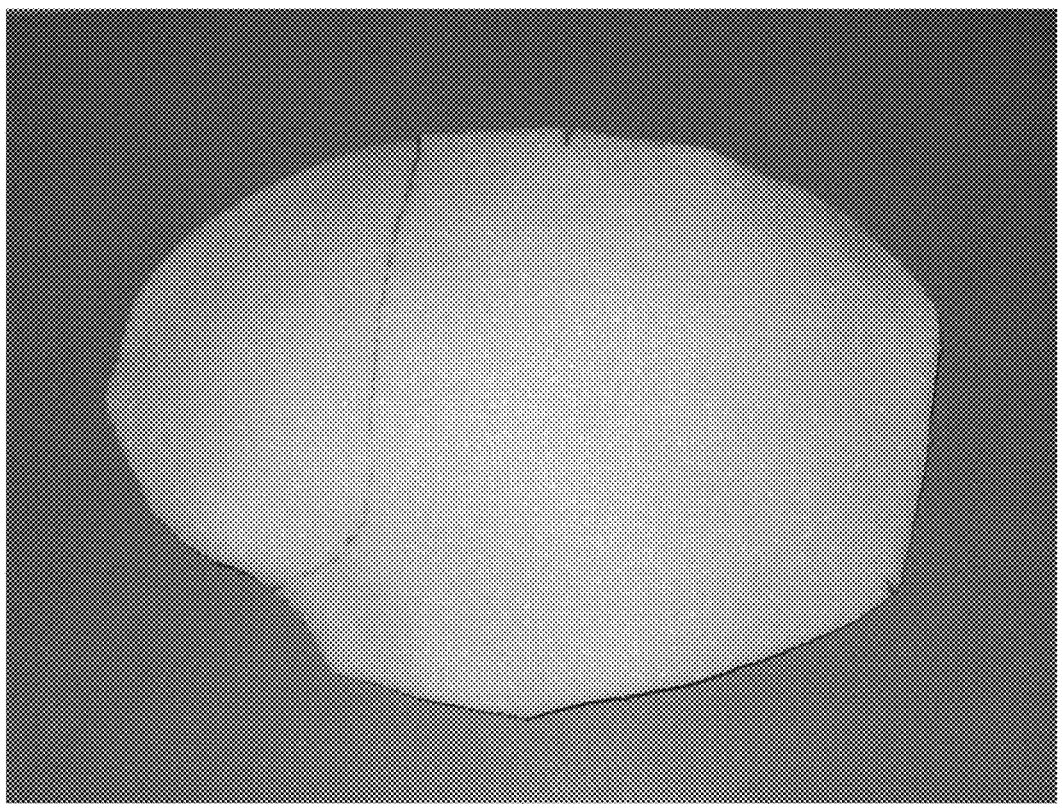
FIG. 6 illustrates a cranial implant made from a thermally bonded porous UHMWPE sheet.

An exemplary cranial implant is shown in FIG. 6. That figure illustrates a porous sheet that has been laminated on one side with a nonporous UHMWPE sheet approximately 0.2 mm thick, then heated and formed to the shape of a section of the human skull. Such an implant may be used to replace a section of the human skull which has been surgically removed due to pathology or trauma. The implant can be trimmed to size by a surgeon during an operative procedure using scissors or shears, and the curvature of the implant can be modified by bending at room temperature by hand or with a hand instrument, such as a bending jig, a mold, or other device.

Figure 7:
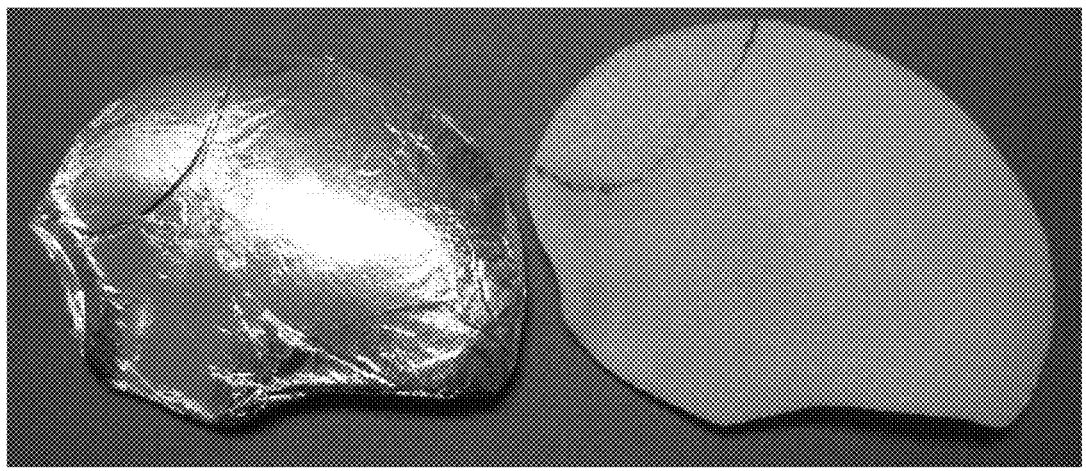
FIG. 7 illustrates the cranial implant of FIG. 6 together with a mold used to form the implant to shape.

FIG. 7 illustrates the aforementioned cranial implant with a mold that may be used to form the implant to shape. The illustrated mold is a rapid prototype made from high temperature polymer in the shape of the desired cranial segment, and covered with aluminum foil. A porous UHMWPE sheet is heated to its softening point, placed over the mold, and manually pressed down to conform the bottom (nonporous) surface to the top of the mold. This process can be automated with a two-sided mold, where the two sides of the mold may be contacted to the sample material so as to place the sample into desired shape.

As an example of these methods, the user may identify an injury site within a subject. The user may then prepare the injury site for implant introduction, e.g., by exposing the injury site, removing excess material from the site, and the like. The user may then install the implant at the desired location. The user may manipulate (e.g., bend, shape) the implant during the procedure so as to conform the implant to the desired form.

The present disclosure also provides methods of applying an implant to a targeted anatomical location. These methods include generating a first shape that substantially matches the shape of a targeted anatomical location; manipulating an implant body comprising a plurality of bonded thermoplastic constituents such that the implant body conforms to the first shape; and installing the implant body at the targeted anatomical location. The implant body may be any implant body according to the present disclosure.

It is not always necessary that the user generate a particular shape before installation and then conform the implant to that shape. A user may alternatively manipulate a body according to the present disclosure such that the implant body substantially conforms to the shape of a targeted anatomical location. The user may then install the implant body at the targeted anatomical location.

The first shape may be generated before the user begins the implantation operation. This may be done by a surgeon, where the surgeon shapes the implant body to conform to the estimated shape of a damaged craniofacial bone that is being replaced. The surgeon may do so with the aid of a scan or other image of the bone being replaced, and, although the implant is advantageously capable of manipulation by hand, may use a mold, bending jig or other tools to assist with shaping the implant.

In some embodiments, the disclosed fibrous materials may include additional elements, such as reinforcing materials.

The reinforcing material may be metal, ceramic, or both, in the form of filaments, mesh, or even particles. These reinforcement materials may be used to enhance a mechanical property of the ijmplant, or to enhance a biological property such as bone ingrowth. Reinforcement materials (e.g., a filament) may have a cross-sectional dimension in the range of from about 0.01 mm to about 1 mm. They may have a length in the range of from about 0.1 mm to about 200 mm, or even an aspect ratio (e.g., for filaments) in the range of from about 5 to about 1000.

The reinforcement materials may represent from about 1% to approximately 50% of an implant by volume, preferably in the range of from about 5% and 30% of an implant by volume. Reinforcements may be evenly distributed throughout the bulk of the porous implant, or may be localized to a particular plane or other region of the implant.

Exemplary reinforcement materials include, for example, 316L stainless steel, titanium, titanium alloys, tantalum, platinum, glass formulations such as bioactive glass 45S5 and bioactive glass 13-93, other silica based glasses, or even boron based bioglass. Class A (osteoproductive) and Class B (osteoconductive) bioglasses are suitable.

The reinforcing materials may also be granules of ceramic or glasses. Such granules may enhance or control tissue ingrowth into the porous materials described herein. A granule suitably has a cross-sectional dimension in the range of from about 0.1 mm to about 1 mm. Granules may be present at a proportion of from 1% to approximately 50% of an implant by volume, preferably in the range of between about 5% and about 30% of the implant by volume. Granules may be evenly distributed throughout the bulk of the porous implant, but may also be concentrated in one plane, surface, or region of the implant. Materials suitable for inclusion as granules include calcium phosphate ceramics, calcium sulfate ceramics, glass formulations such as 45S5, 13-93, silica based glasses, and boron based bioglass.

The reinforcement materials may be incorporated into the disclosed materials during molding or heating. For example, a user may introduce a quantity of UHMWPE filaments into a mold, add a reinforcement material (e.g., titanium filaments), and then add additional UHMWPE filaments atop the reinforcement followed by heating the mold so as to form a fibrous material that includes the titanium filaments as reinforcements. The reinforcement material may be disposed such that at least some of the reinforcement material is exposed to the environment exterior to an implant. For example, a user may place a number of reinforcing titanium fibers (or glass granules) into a mold followed by introducing UHMWPE filaments atop the fibers and then processing the filaments and fibers so as to bond the filaments to one another.

Exemplary Embodiments

The following embodiments are illustrative only and do not limit the scope of the present disclosure.

In a first exemplary embodiment, a user turned fibers from UHMWPE (round bar), HDPE (round bar), Radel™ (a polyphenylsulfone), and PMMA on a lathe. The fibers had a diameter in the range of from about 0.1 to about 0.7 mm.

The UHMWPE fibers had a diameter of about 0.25 mm, and were then cut to lengths of about 15-20 mm by hand. About 18 g of the fibers were packed into a mold having a cavity size of 8 cm by 8 cm; the fibers were packed to a depth of about 6 mm of a 14 mm frame height. The fibers has a cross-section of about 0.25 mm×0.5 mm.

The fibers were then heated in a vacuum oven at about 200° C. for about 3 hours. A UHMWPE film was skived and annealed at 230° C. in a Carver Press unit for 2 minutes and then cooled between fan plates. A film was then melted to the first melted fiber sample in a Carver Press at 230° C. for 2 minutes.

HDPE fibers having a diameter of from about 0.25 to about 0.5 mm and a length of from about 15 to 20 mm were processed for 30-45 mintues in an vacuum oven in a 5 cm×5 cm aluminum mold with C-clamps, and b-tricalcium phosphate (bTCP) was added for processability. Processing these fibers at 200° C. for 25-30 minutes yielded well-fused samples having a range of pore sizes.

In second exemplary embodiment, UHMWPE fibers were created on a CNC (computer numerical control) mill. The fibers were about 3 mm to 10 mm in length and about 0.5×0.5 to 0.5×0.05 mm in cross-section. The cross-section of at least some of the fibers varied along the length of the fiber. About 63 g of these fibers were packed into a 20×14×0.4 cm mold. The mold was heated in a 225° C. Carver Press for about 10 minutes. The mold was then air cooled. Skived UHMWPE film was annealed in a 220° C. vacuum oven, and the annealed film and porous structure were then laminated in the Carver Press (one platen at 230° C.) for about one minute and then air cooled.

UHMWPE fibers and a UHMWPE film were also examined. In these experiments, a film was annealed to a fiber-containing sample at 230° C. in a Carver Press device. In one approach, a contoured mold bottom was heated to 230° C. using cartridge heaters. A UHMWPE fiber sample was placed atop a UHMWPE film, which was then in turn placed atop a PTFE film. The assembly was then placed inside a contoured mold, with mold platens heated to 120° C. and 230° C.

A user may also form a bonded structure with high porosity by heating fibers in a heated oven so as to form a sheet. The resultant sheet may be placed into a Carver press and then pressed under additional heating so as to further compact the sheet. This compaction in turn reduces the porosity of the sheet and increases the sheet's density.

The following results are illustrative only and should not be understood as limiting the scope of the present disclosure in any way.

The flexural and tensile properties of fibrous porous UHMWPE strips made according to the present disclosure were investigated. Samples of 3 mm thick fibrous porous polyethylene (F-PPE), 4 mm thick F-PPE, and 3 mm thick SynPOR™ (porous polyethylene made from melt bonded particles) were tested for tensile properties, flexural properties, and porosity by mercury intrusion porosimetry. The test procedures involved testing UHMWPE strips (formed from fused UHMWPE filaments) having dimensions of about 10×50×3 mm. The test samples were created on a CNC mill as described above. These test samples were made according to the procedures described in connection with the second exemplary embodiment above, but were molded in a 80 mm×80 mm×3 mm mold. The mold was heated in vacuum oven at about 225° C. Mechanical testing was performed using an Instron Universal Testing Machine. Flexural bending test calculations were based on ASTM D6272 and axial tensile test calculations were based on ASTM D638M. Porosimetry testing was done per ISO 15901-1:2005, using an Autopore IV Mercury Porosimetry System.

The tests involved control samples machined from commercially-available SynPOR™ material, which is a material manufactured from an inert, nonabsorbable polymer (UHWMPE) that is formulated to contain a network of open and interconnecting pores approximately 100-250 μm in size. The controls were 50×50×3 mm sheets. The test samples were 3 mm and 4 mm thick fibrous porous UHMWPE sheets.

Test samples were formed from filaments similar to those illustrated in FIG. 2, the filaments being approximately 0.5×0.5 mm at the large end and approximately 0.5 mm thick along the length; all samples that underwent mechanical testing were made with filament/chips made by a milling process. SynPOR™ controls were made of UHMWPE particles that were essentially cuboid in shape, with a size of about 0.4×0.4×0.4 mm. The SynPOR™ control samples did not contain any metal titanium mesh; all samples (control and test samples) were made from polyethylene only.

For flexural testing, the width and thickness of each specimen were measured, and these values used for flexural strength and modulus calculations as follows.

Flex. Strength(MPa)=$(3 \times P \times L)/(4 \times w \times t^2)$ where P=load (N)
L=support span (mm)
w=width (mm)
t=thickness (mm)
Flex. Modulus (MPa)=$(0.17 \times L^3 \times m)/(w \times t^3)$
where L=support span (mm)
m=slope (N/mm)
w=width (mm)
t=thickness (mm)

The crosshead speed of the tests was about 5 mm/min, and the samples were tested in a 4-point bending fixture. The supports for the testing apparatus has a diameter of about 5 mm, with a support span of about 30 mm, and a load span of about 15 mm. The flexural tests were repeated for six specimens.

Tensile testing was also performed; the width and thickness of each specimen were measured and then these values were used for tensile strength and modulus calculations. The calculations were performed as follows:

Tensile Strength(MPa)=max. $P/(w \times t)$ where P=load (N)
w=width (mm)
t=thickness (mm)

Tensile modulus(MPa)=(difference in stress)/(difference in strain)

The crosshead speed was about 5 mm/min, with a distance of about 30 mm between tensile grips. These tests were repeated for 6 test specimens. The results of these tests are set forth in FIGS. 8, 9, 10, and 11 and in the data tables below:

| Porosimetry | | |
| --- | --- | --- |
| | intrusion vol. (ml/g) by Hg intrusion | % solids |
| SynPOR 3 mm thick | 0.46 | 57% |
| Fibrous 3 mm thick | 0.68 | 36% |
| Fibrous 4 mm thick | 0.54 | 49% |

| Tensile | | | | |
| --- | --- | --- | --- | --- |
| | Tensile Strength (Mpa) | Tensile Modulus (Mpa) | normalized tensile strength (Mpa) | normalized tensile modulus (Mpa) |
| SynPOR 3 mm | 2.99 | 267.2 | 5.28 | 472.8 |
| Fibrous 3 mm | 3.24 | 154.2 | 9.08 | 431.5 |
| Fibrous 4 mm | 5.03 | 247.2 | 10.26 | 505.0 |

| Flexural | | | | |
| --- | --- | --- | --- | --- |
| | Flexural Strength (Mpa) | Flexural Modulus (Mpa) | normalized flexural strength (Mpa) | normalized flexural modulus (Mpa) |
| SynPOR 3 mm | 4.86 | 170.8 | 8.59 | 302.1 |
| Fibrous 3 mm | 4.45 | 137.6 | 12.46 | 384.9 |
| Fibrous 4 mm | 7.83 | 233.0 | 15.99 | 475.8 |

Analysis of these data reflected the fact that the three test samples were of varying porosity. In order to evaluate the effects of processing and structural parameters on mechanical strength independent of porosity, the mechanical data was normalized based on the percentage of solid structure (i.e., 1-% porosity) in the samples. This effectively controls for the varying amount of void space in the samples from the calculations, and allows comparison of the mechanical properties of the remaining solid structure. The 3 mm SynPOR product was the least porous of the materials tested and the 3 mm F-PPE sample was most porous.

Non-normalized data indicate that the 3 mm SynPOR was slightly higher than the disclosed materials in flexural strength, flexural modulus, and tensile modulus, and insignificantly higher in tensile strength relative to the 3 mm F-PPE. If, however, the data are normalized for porosity, the 3 mm F-PPE demonstrated higher tensile strength, flexural strength, and flexural modulus than the 3 mm SynPOR product. Data were similar for the 4 mm thick sample materials in comparison to 3 mm SynPOR controls. Without being bound to any particular theory, the performance differences between 3 mm and 4 mm F-PPE samples may be an effect of sample geometry, not a fundamental difference in structure.

Figure 8:
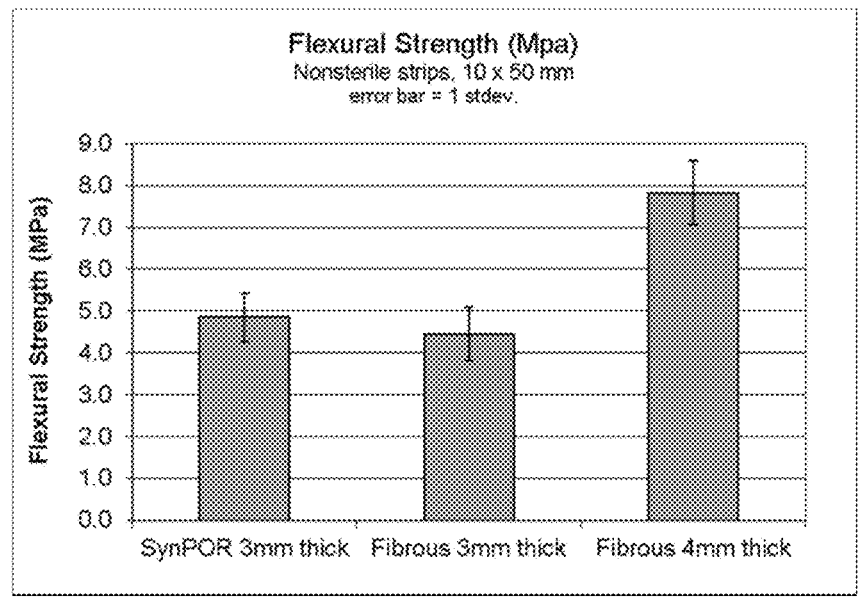
FIG. 8 illustrates flexural strength data for control materials and for samples according to the present disclosure.
Figure 8:
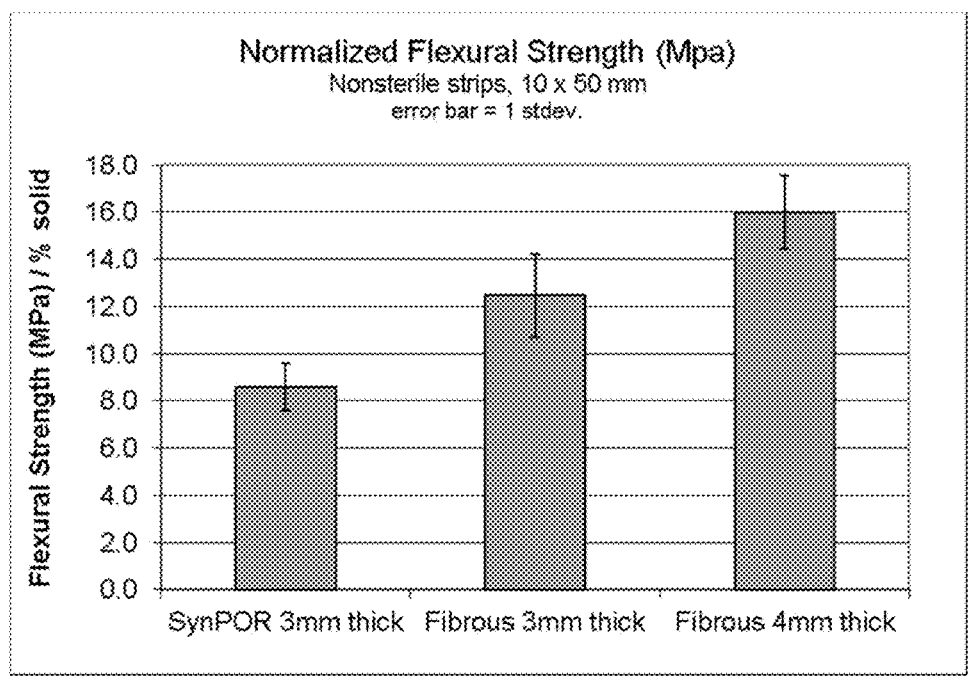

FIG. 8 illustrates flexural strength data from the above-described test samples and SynPOR controls. As can be seen in the bottom panel of the figure, test samples having a thickness of 3 mm and 4 mm exhibited a higher normalized flexural strength than did SynPOR control samples of 3 mm thickness. The differences in non-normalized flexural strength between the control and test samples were, as explained above, affected by the porosity of the samples, and the data have been re-analyzed and adjusted based on porosity. Without being bound to any single theory, the differences in strength and modulus in the original data may be due more to porosity than to the samples' microscopic structure.

Figure 9:
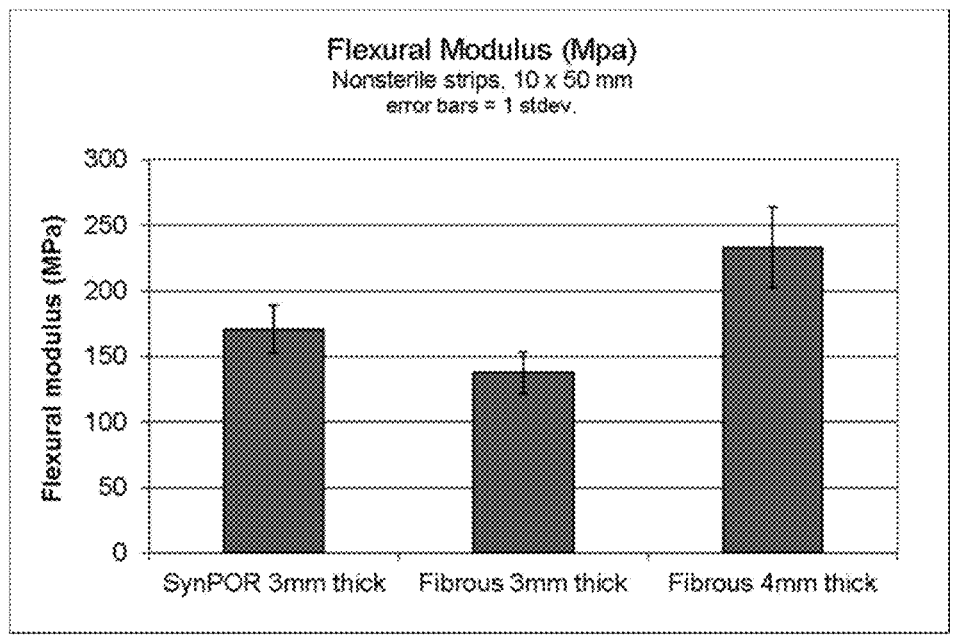
FIG. 9 illustrates flexural modulus data for control materials and for samples according to the present disclosure.
Figure 9:
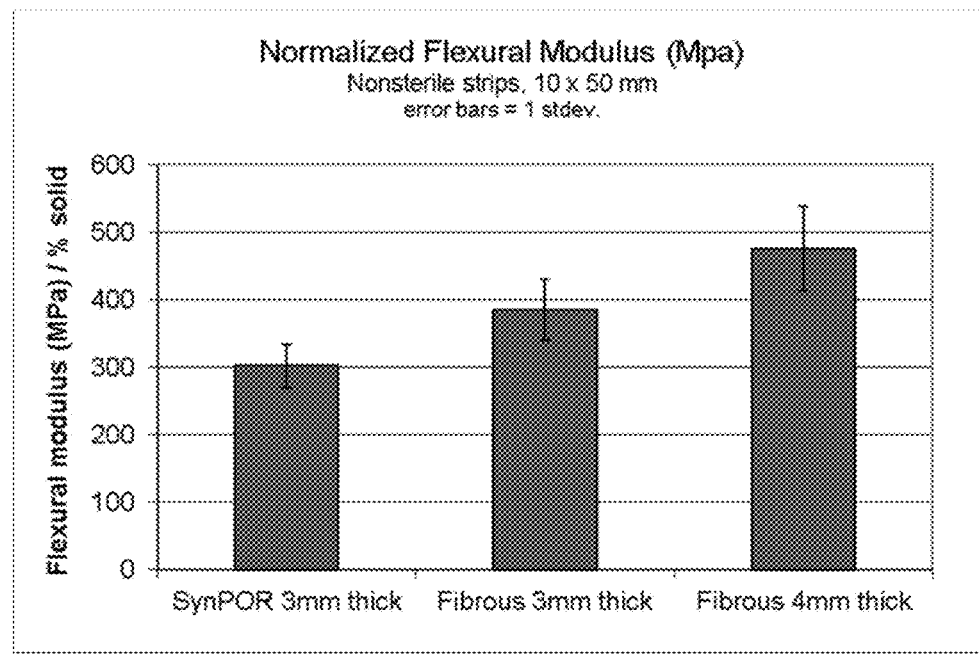

FIG. 9 illustrates flexural modulus data for SynPOR control samples and for 3 mm and 4 mm thick test samples. As seen in the figure, test samples having a thickness of 3 mm and 4 mm exhibited a higher normalized flexural modulus than did SynPOR control samples of 3 mm thickness. The differences in non-normalized flexural modulus between the control and test samples may be, as explained above, affected by the porosity of the samples, and the data have been re-analyzed and adjusted based on porosity.

Figure 10:
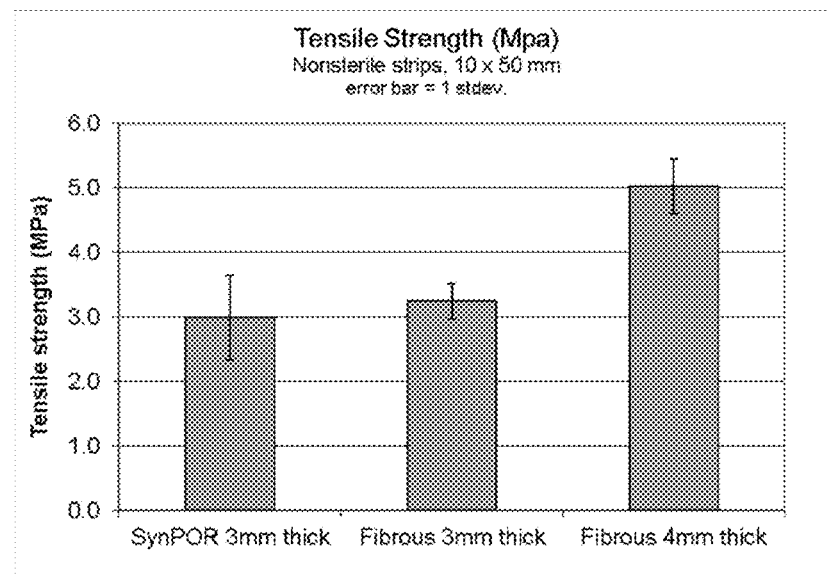
FIG. 10 illustrates tensile strength data for control materials and for samples according to the present disclosure.
Figure 10:
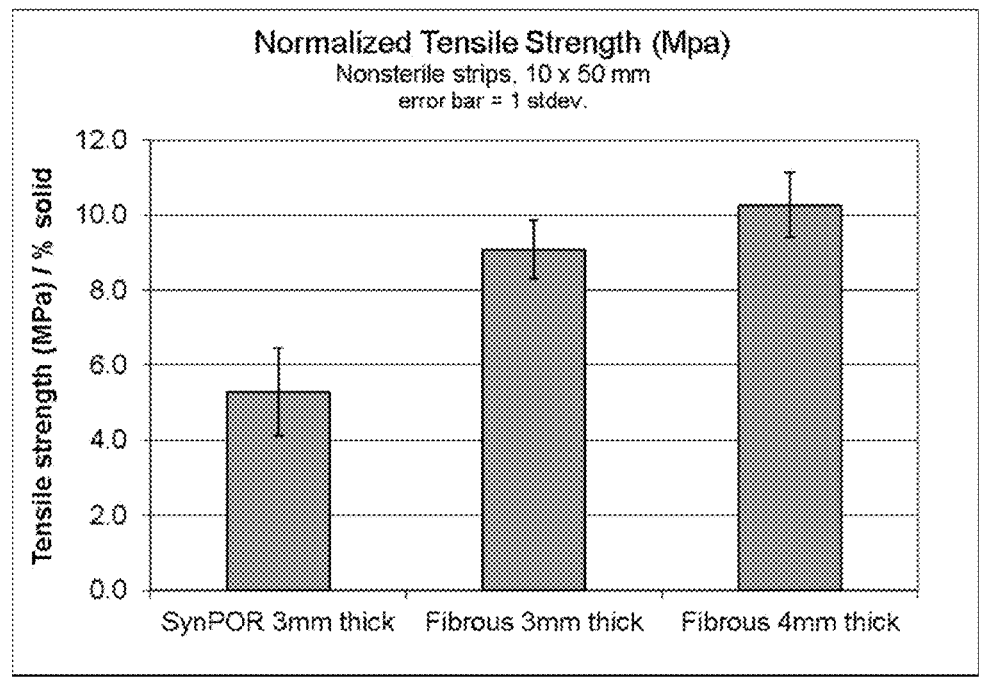

FIG. 10 illustrates tensile strength data from the above-described test samples and SynPOR controls. As can be seen in the bottom panel of the figure, test samples having a thickness of 3 mm and 4 mm exhibited a higher normalized tensile strength than did SynPOR control samples of 3 mm thickness. The differences in non-normalized flexural strength between the control and test samples may be, as explained above, affected by the porosity of the samples.

Figure 11:
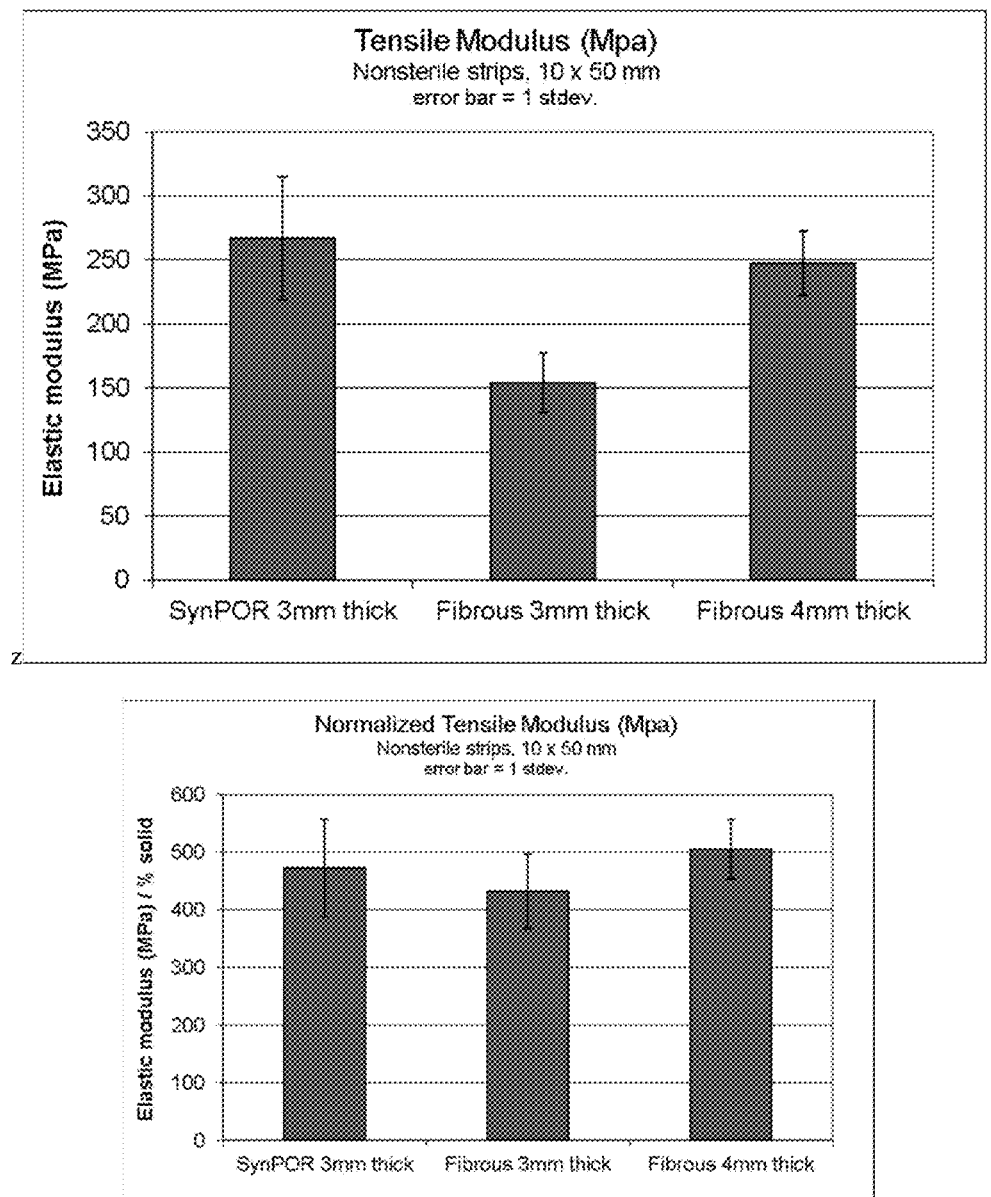
FIG. 11 illustrates tensile modulus data for control materials and for samples according to the present disclosure.

FIG. 11 illustrates tensile modulus data from the above-described test samples and SynPOR controls. As can be seen in the bottom panel of the figure, test samples having a thickness of 3 mm and 4 mm exhibited a higher normalized tensile strength than did SynPOR control samples of 3 mm thickness.

What is claimed:

1. A orthopedic implant to augment or replace a section of bone of a patient, comprising:
   a porous body consisting essentially of a plurality of randomly arranged and entangled thermoplastic constituents having a length in the range of about 3 mm to about 50 mm;
   wherein the plurality of thermoplastic constituents are fibers, filaments, or a combination thereof;
   wherein the randomly arranged and entangled thermoplastic constituents have an average aspect ratio in the range of about 2 to about 1000 and are bonded to other thermoplastic constituents at multiple sites;
   wherein the porous body has a thickness in the range of about 1 mm to about 50 mm;
   wherein the porous body has a porosity gradient such that a first region of the porous body has a first porosity that is greater than a second porosity of a second region of the porous body;
   wherein the porous body has a normalized tensile strength in the range of about 5 MPa to about 15 MPa;
   wherein the porous body has a normalized tensile modulus in the range of about 300 MPa to about 600 MPa;
   wherein the porous body has a normalized flexural strength in the range of about 5 MPa to about 25 MPa;
   wherein the porous body has a normalized flexural modulus in the range of about 250 MPa to about 600 MPa; and
   wherein the thermoplastic constituents comprise polyethylene, a copolymer of polyethylene, or mixtures or blends thereof.

2. The orthopedic implant of claim 1, wherein the randomly arranged and entangled thermoplastic constituents allow the porous body to be manipulated at room temperature from a first shape to a second shape and maintain the second shape at about internal body temperature.

3. The orthopedic implant of claim 1, wherein the porous body has an interconnected porosity.

4. The orthopedic implant of claim 1, wherein the porous body has a porosity in the range of from about 10% to about 70% by volume.

5. The orthopedic implant of claim 1, wherein the biocompatible implant has a thickness in the range of from about 1 mm to about 10 mm.

6. The orthopedic implant of claim 1, wherein at least some of the randomly arranged and entangled thermoplastic constituents have an average cross-sectional dimension in the range of from about 0.1 mm to about 1 mm.

7. The orthopedic implant of claim 1, wherein the randomly arranged and entangled thermoplastic constituents have a length in the range of 2 mm to 20 mm.

8. The orthopedic implant of claim 1, wherein the randomly arranged and entangled thermoplastic constituents have a length in the range of 3 mm to 10 mm.

9. The orthopedic implant of claim 1, wherein the average aspect ratio of the randomly arranged and entangled thermoplastic constituents is in the range of 5 to about 500.

10. The orthopedic implant of claim 1, wherein the average aspect ratio of the randomly arranged and entangled thermoplastic constituents is in the range of from 5 to 50.

11. The orthopedic implant of claim 2, wherein said polyethylene comprise high density polyethylene, ultrahigh molecular weight polyethylene, or a mixture thereof.

12. The orthopedic implant of claim 1, wherein the second region is a non-porous region.

13. The orthopedic implant of claim 1, wherein the implant consists essentially of the porous body bonded to another material.

14. A orthopedic implant to augment or replace a section of bone of a patient, comprising:
   a porous body comprising a plurality of randomly arranged and entangled polyethylene fibers or filaments having a length in the range of about 3 mm to about 50 mm;
   wherein the randomly arranged and entangled polyethylene fibers or filaments have an average aspect ratio in the range of about 2 to about 1000 and are bonded to other polyethylene fibers or filaments at multiple sites;

wherein the porous body has a porosity gradient such that a first region of the porous body has a first porosity that is greater than a second porosity of a second region of the porous body;

wherein the porous body has a thickness in the range of about 1 mm to about 5 mm;

wherein the porous body has a normalized tensile strength in the range of about 5 MPa to about 15 MPa;

wherein the porous body has a normalized tensile modulus in the range of about 300 MPa to about 600 MPa;

wherein the porous body has a normalized flexural strength in the range of about 5 MPa to about 25 MPa;

wherein the porous body has a normalized flexural modulus in the range of about 250 MPa to about 600 MPa; and wherein the porous body is devoid of metal.

15. The orthopedic implant of claim 14, wherein the implant consists essentially of the porous body bonded to another material.

* * * * *